US009757332B2

(12) United States Patent
Kitanaka et al.

(10) Patent No.: US 9,757,332 B2
(45) Date of Patent: Sep. 12, 2017

(54) GEL-LIKE COMPOSITION HAVING HIGH UBIQUINOL CONTENT

(71) Applicant: UHA Mikakuto Co., Ltd., Yamatokooriyama-shi (JP)

(72) Inventors: Shinsuke Kitanaka, Yamatokooriyama (JP); Yoshimi Haza, Yamatokooriyama (JP); Satoshi Doi, Yamatokooriyama (JP); Yasuhiro Shinka, Yamatokooriyama (JP); Nobuya Sato, Yamatokooriyama (JP); Akinobu Kishi, Yamatokooriyama (JP); Taiji Matsukawa, Yamatokooriyama (JP); Takeki Matsui, Yamatokooriyama (JP); Yasumasa Yamada, Yamatokooriyama (JP); Ichiro Yamada, Yamatokooriyama (JP)

(73) Assignee: UHA MIKAKUTO CO., LTD., Yamatokooriyama-shi (JP)

( * ) Notice: Subject to any disclaimer, the term of this patent is extended or adjusted under 35 U.S.C. 154(b) by 0 days.

(21) Appl. No.: 14/892,031

(22) PCT Filed: Apr. 30, 2014

(86) PCT No.: PCT/JP2014/062027
§ 371 (c)(1),
(2) Date: Nov. 18, 2015

(87) PCT Pub. No.: WO2014/188861
PCT Pub. Date: Nov. 27, 2014

(65) Prior Publication Data
US 2016/0089332 A1 Mar. 31, 2016

(30) Foreign Application Priority Data

May 20, 2013 (JP) ................................ 2013-105898
Nov. 29, 2013 (JP) ................................ 2013-247838
Apr. 25, 2014 (JP) ................................ 2014-091856

(51) Int. Cl.
*A61K 9/10* (2006.01)
*A23G 3/36* (2006.01)
(Continued)

(52) U.S. Cl.
CPC .................. *A61K 9/10* (2013.01); *A23G 3/36* (2013.01); *A23G 3/364* (2013.01); *A23G 3/368* (2013.01);
(Continued)

(58) Field of Classification Search
CPC . A23G 3/368; A23G 3/44; A23G 3/48; A23G 3/50; A23G 3/364; A23G 3/36;
(Continued)

(56) References Cited

U.S. PATENT DOCUMENTS

2008/0226710 A1  9/2008  Fantuzzi
2010/0061969 A1* 3/2010  Otsubo ................ A21D 2/14
                                                        424/94.1
2010/0279413 A1* 11/2010 Fain ..................... A61K 31/122
                                                        435/406

FOREIGN PATENT DOCUMENTS

JP         2922017 B2    7/1999
JP         2005-43 A1    1/2005
(Continued)

OTHER PUBLICATIONS

Kishida et al. (WO 2008035757 A1, Google ENG. Trans. Used, 2008.*
(Continued)

*Primary Examiner* — Blessing M Fubara
(74) *Attorney, Agent, or Firm* — Kratz, Quintos & Hanson, LLP

(57) ABSTRACT

This invention relates to a gel-like composition in which ubiquinol is dispersed and stabilized in a gel and which
(Continued)

contains 0.2 to 5% by weight of ubiquinol, 5 to 15% by weight of gelatin, 55 to 80% by weight of carbohydrate and/or water-soluble dietary fiber, and 9 to 18% by weight of water, and further contains ascorbic acid and/or gallate type catechin.

12 Claims, 2 Drawing Sheets

(51) Int. Cl.

| | |
|---|---|
| A23G 3/42 | (2006.01) |
| A23L 3/3544 | (2006.01) |
| A61K 31/09 | (2006.01) |
| A61K 47/36 | (2006.01) |
| A61K 9/00 | (2006.01) |
| A61K 9/48 | (2006.01) |
| A23L 29/231 | (2016.01) |
| A23L 33/21 | (2016.01) |
| A23G 3/44 | (2006.01) |
| A23G 3/48 | (2006.01) |
| A23G 3/50 | (2006.01) |
| A61K 9/06 | (2006.01) |
| A61K 9/16 | (2006.01) |
| A61K 47/10 | (2017.01) |
| A61K 47/12 | (2006.01) |
| A61K 47/42 | (2017.01) |
| A23L 29/281 | (2016.01) |
| A23L 33/10 | (2016.01) |

(52) U.S. Cl.
CPC .................. *A23G 3/42* (2013.01); *A23G 3/44* (2013.01); *A23G 3/48* (2013.01); *A23G 3/50* (2013.01); *A23L 3/3544* (2013.01); *A23L 29/231* (2016.08); *A23L 29/284* (2016.08); *A23L 33/10* (2016.08); *A23L 33/21* (2016.08); *A61K 9/0056* (2013.01); *A61K 9/0095* (2013.01); *A61K 9/06* (2013.01); *A61K 9/16* (2013.01); *A61K 9/4858* (2013.01); *A61K 31/09* (2013.01); *A61K 47/10* (2013.01); *A61K 47/12* (2013.01); *A61K 47/36* (2013.01); *A61K 47/42* (2013.01); *A23V 2002/00* (2013.01)

(58) Field of Classification Search
CPC ....... A23G 3/42; A23L 29/231; A23L 29/284; A23L 33/10; A23L 33/21; A23L 3/3544; A61K 9/10; A61K 9/06; A61K 9/0056; A61K 9/4858; A61K 9/16; A61K 47/10; A61K 47/12; A61K 47/36; A61K 47/42; A61K 31/09; A23V 2002/00
See application file for complete search history.

(56) References Cited

FOREIGN PATENT DOCUMENTS

| | | |
|---|---|---|
| JP | 3742602 B2 | 2/2006 |
| JP | 3790530 B2 | 6/2006 |
| JP | 2007-507427 A1 | 3/2007 |
| JP | 3892881 B2 | 3/2007 |
| JP | 2007-526303 A1 | 9/2007 |
| JP | 4361706 B2 | 11/2009 |
| JP | 2010-124745 A1 | 6/2010 |
| JP | 2010-527905 A1 | 8/2010 |
| JP | 2010-530904 A1 | 9/2010 |
| JP | 5015548 B2 | 8/2012 |
| JP | 5103188 B2 | 12/2012 |
| JP | 5421674 B2 | 2/2014 |
| WO | WO 03/062182 A1 | 7/2003 |
| WO | WO 2007/148798 A1 | 12/2007 |
| WO | WO 2008/035757 A1 | 3/2008 |

OTHER PUBLICATIONS

EPC Europe GMBH (JP2010527905A1, Google ENG. Trans. Used), 2010.*
VESIsorb, copyright 2005.*
R. Takano; "Computer-based simulation," Drug Delivery System; 25-4; 2010; pp. 362-370 (9 Sheets)/p. 7 of specification.
K. Hosoe, et al.; "Study on safety and bioavailability of ubiquinol (Kaneka QH TM) after single and 4-week multiple oral administration to healthy volunteers," Regulatory Toxicology and Pharmacology; vol. 47; 2007; pp. 19-28 (10 Sheets)/p. 7 of specification.
H. Wada, et al.; "Redox Status of Coenzyme Q10 is Associated With Chronological Age;" Journal of American Society; vol. 55; No. 7; Jul. 2007; pp. 1141-1142 (2 Sheets)/p. 7 of specification Geriatrics.
International Search Report for International Application No. PCT/JP2014/062027 dated Aug. 5, 2014.

* cited by examiner

[Fig. 1]
Fig. 1 Change amount of ubiquinol concentration in blood
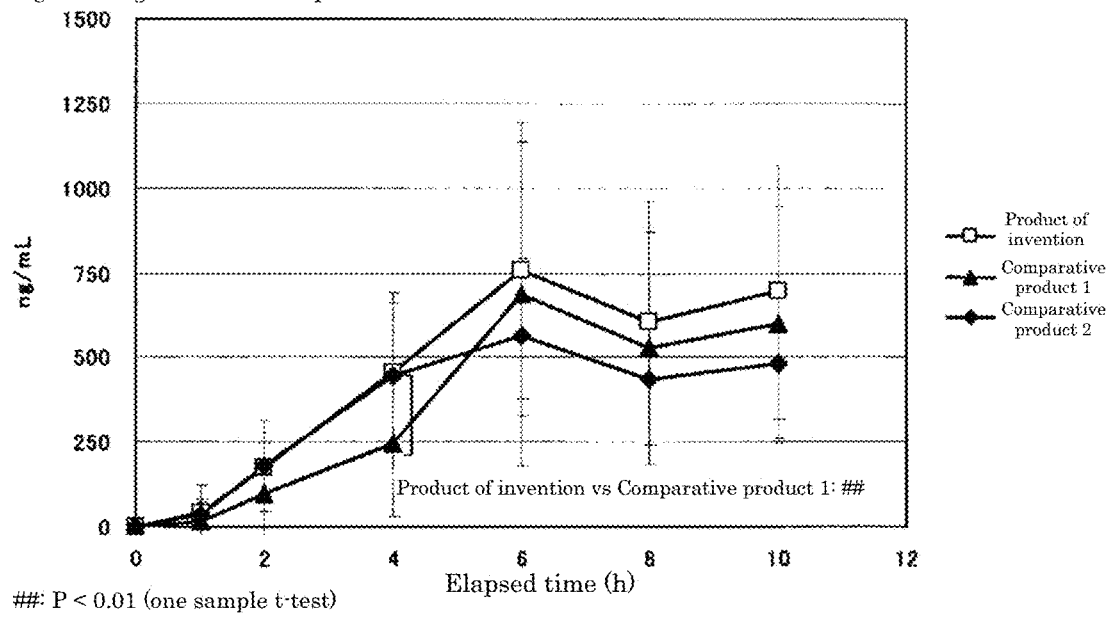
: $P < 0.01$ (one sample t-test)
[Fig. 2]
Fig. 2 Ubiquinol change amount in blood $AUC_{0-10h}$
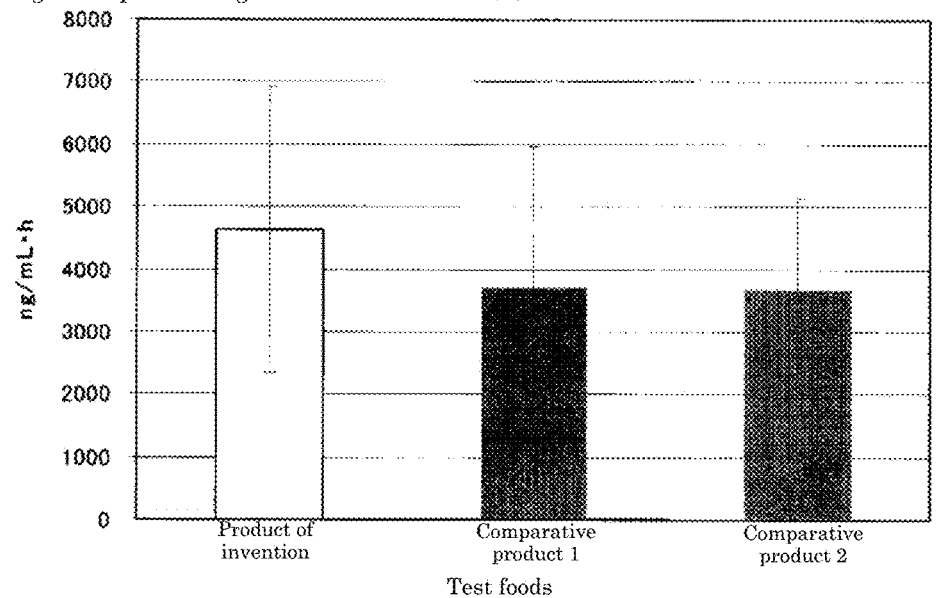

[Fig. 3]
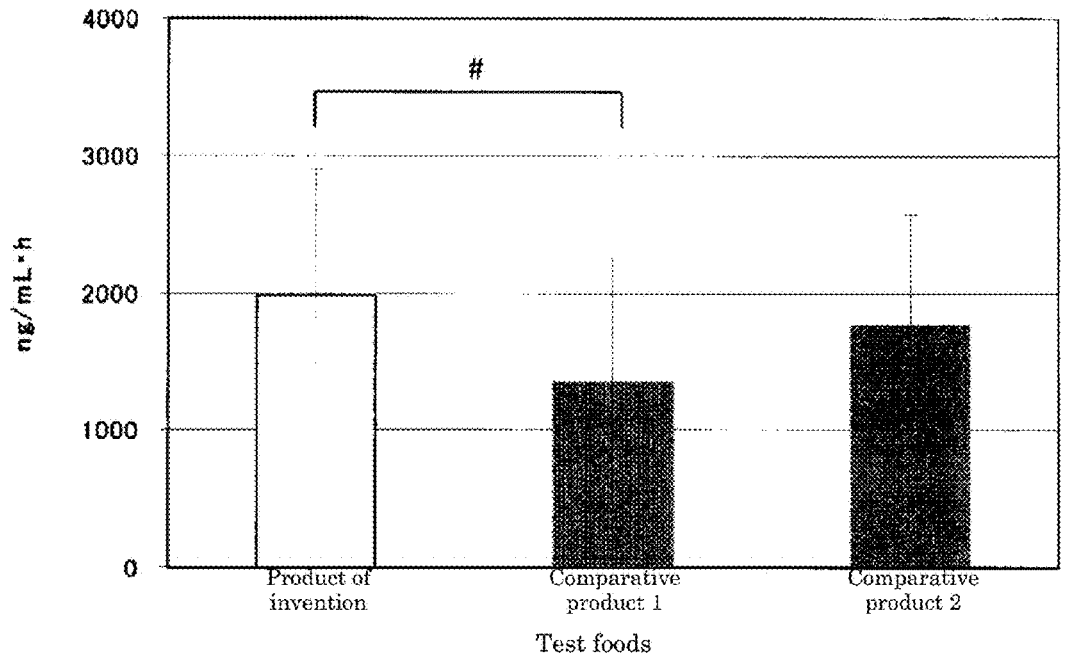
Fig. 3 Ubiquinol change amount in blood $AUC_{0-6h}$
\#: $P < 0.05$ (one sample t-test)
[Fig. 4]
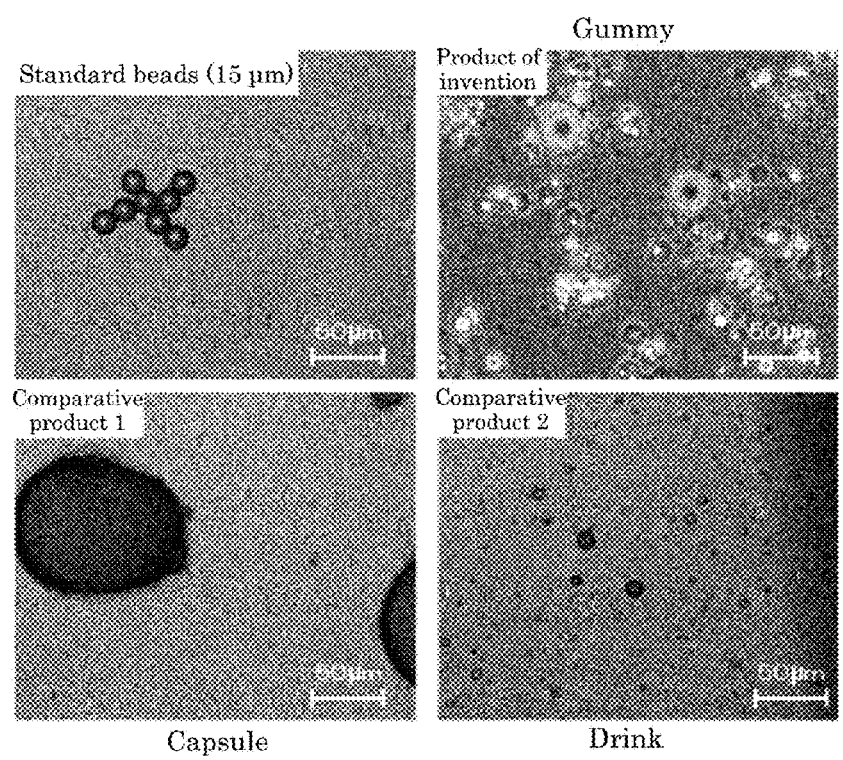

GEL-LIKE COMPOSITION HAVING HIGH UBIQUINOL CONTENT

TECHNICAL FIELD

The present invention relates to a gel-like composition containing a high content of ubiquinol and a method for producing the same.

BACKGROUND ART

The ubiquinol (which is also referred to as a reduced coenzyme Q10, a reduced CoQ10, and a reduced form coenzyme Q10) is a strong antioxidative component and is a functional substance widely used in supplements for preventing cardiac diseases and the like all over the world.

The utilization efficiency of the ubiquinol in the body is higher than that of ubiquinone (oxidized coenzyme Q10) which is an oxidation form of the ubiquinol. Therefore, a supplement of the ubiquinol is dealt with a high price nearly twice the price of a supplement of the ubiquinone. The ubiquinol, however, is likely to be oxidized to ubiquinone due to oxygen and the like in the air, and thus is a very unstable substance, which has made it difficult to stably blend the ubiquinol in a supplement.

Heretofore, some methods for stabilizing the ubiquinol are known (Patent Documents 1 to 6).

Patent Documents 1 to 3 describe methods for causing a surfactant (for example, emulsifier) to coexist in ubiquinol. However, when a large amount of the ubiquinol is blended in foods and cosmetics, it is necessary to increase the addition amount of an emulsifier in connection with the increase in the ubiquinol, which has great influence on the physical properties, the taste, and the cost of the foods and the cosmetics. Moreover, consumers highly interested in health and beauty tend to strongly prefer natural raw materials, and thus it is expected that the consumers do not prefer the use of food additives such as an emulsifier.

Patent Documents 4 and 5 describe a method for stabilizing ubiquinol by blending citric acid and ascorbic acid. However, it cannot be said that the stability of ubiquinol is sufficient in these inventions (For example, when ubiquinol and citric acid or ascorbic acid were mixed, and then the mixture was allowed to stand still in the air at 25° C. for 4 days, the weight ratio of ubiquinol/ubiquinone was smaller than 90/10.) and the inventions do not have an effect of uniformly dispersing ubiquinol in an aqueous solution, and therefore the inventions cannot be applied to a water dispersible supplement.

Patent Document 6 describes a particle-like composition in which an oil-based component containing ubiquinol is dispersed in a water-soluble diluent. Although the particle-like composition obtained by the above-described invention has high reduced retention and oral absorbability, an emulsification process by a high-pressure homogenizer and a drying process such as spray dry are required, so that special facilities and cost are required. Moreover, for one having high reduced retention in Examples, the use of an emulsifier is indispensable. Moreover, the invention described above requires performing drying until the recovery in a particle state can be achieved. Accordingly, the remaining moisture amount is usually preferably 30% by weight or less, more preferably 10% by weight or less, and most preferably 5% by weight or less of the particle weight after the recovery.

Moreover, the ubiquinol has low solubility in water and thus easily causes crystallization and separation in water. Therefore, it has been more difficult to blend the ubiquinol in a water dispersible supplement in a high proportion.

In general, it is said that a water insoluble functional substance has low absorbability into the body. For example, a supplement having high dispersibility in water in which the absorbability into the body is increased by water-solubilizing or emulsifying the water insoluble functional substance has drawn attention. Also with respect to the ubiquinol having low solubility in water, a development of a technique of stably blending the ubiquinol in the water dispersible supplement in a high proportion has been long awaited.

In particular, pharmaceutical compounds and functional components to be blended in pharmaceutical agents and supplements are mostly fat-soluble substances. However, when orally taken, the fat-soluble substances difficult to dissolve in digestive organs. Therefore, it is generally known that the fat-soluble substances have low absorbability into the body of humans (Non-patent Document 1). Accordingly, increasing the absorption efficiency of the useful fat-soluble substances is a useful means for increasing the bioavailability. Thus, a large number of techniques have been developed, e.g., a means of processing a fat-soluble substance into a stable emulsified state with an emulsifier (Patent Document 7), a means of increasing the absorption efficiency by the use of an emulsifier and oil in combination (Patent Document 8), a means of controlling the particle size to the optimal particle system, such as fine particle size, as in a nano-emulsion (Patent Document 9), and a means of increasing the absorption efficiency by a drug delivery system (hereinafter referred to as "DDS") of liposome and the like, and further preventing inconvenient decomposition (Patent Document 10).

The ubiquinol (functional component which is also referred to as a reduced coenzyme Q10) which is a fat-soluble substance is an active coenzyme Q10 which acts in the living body and is blended in dietary supplements and widely sold in advanced nations, mainly in the United States, as a component effective for preventing and treating cardiac diseases. However, there is a report of a clinical test that the absorbability of the ubiquinol into the body is low particularly in oral intake, and only about several percentages of the intake amount is absorbed into blood and the ubiquinol is mostly discharged (Non-patent Document 2). In usual, a general dosage form of the fat-soluble substance supplement is encapsulating the fat-soluble substance in a soft capsule in terms of the stability of components, the storageability and portability of products, and the ease of oral intake. In particular, in order to improve the absorption efficiency even just a little, a technique of encapsulating ubiquinol emulsified with an emulsifier or the like in a soft capsule is also known (Patent Document 11).

In order to encapsulate the fat-soluble substance in a soft capsule, it is usually necessary to dissolve the fat-soluble substance in oils and fats, such as vegetable oils and fats, or make the fat-soluble substance turbid in the form of slurry. Moreover, it is necessary to add an emulsifier, such as lecithin or sucrose fatty acid ester, for the purpose of homogenization. In particular, advanced emulsification processing is required to increase the absorbability and it is necessary to use a large amount of a plurality of emulsifiers or perform advanced processing (Patent Document 12).

However, the internal volume of one soft capsule is limited, and therefore the blending amount is limited when a large amount of a fat-soluble substance is blended in a stable emulsified state. Moreover, when the required intake amount of the target fat-soluble substance is large, the number of soft capsules to be taken also increases, which is a heavy burden on a user. Therefore, in order to blend a large amount of the fat-soluble substance, it cannot be said that the demand is sufficiently satisfied by the dosage form of the soft capsule. In particular in the United States, the intake amount of the ubiquinol is large and a supplement which is recommended to take by 400 mg/day or more as a coenzyme Q10 also increases. In this case, the number of the supplements to be taken is large or one particle size is large, which makes it difficult for a user to drink the same and further the burden of a user when supplements of other functional components are taken together is immeasurable. Therefore, a dosage form which allows blending of the ubiquinol in a high concentration, a dosage form which is not difficult to take a large amount of the ubiquinol, and also a dosage which allows intake without water at any time and at any place have been demanded.

In supplements aiming at health maintenance and health improvement and prevention of diseases, it is ideal to avoid the use of emulsifiers, such as oils and fats and fatty acid esters, as much as possible but it is ironical that lipid and emulsifiers need to be simultaneously taken in in order to take the fat-soluble functional component. Moreover, there is a tendency that health-conscious consumers do not prefer the emulsifier which is one of the raw materials from the viewpoint of palatability. In actual, there are a large number of products indicating "fat free" and "emulsifier free" as a feature and the products are supported by a large number of consumers.

As described above, in order to improve the absorbability of the fat-soluble functional component, such as ubiquinol, into the body, it is usually necessary to dissolve the fat-soluble functional component in oils and fats and further to obtain the fat-soluble functional component in a stable emulsified state using an emulsifier, however, on the other hand, there are also consumer needs, such as "fat free" and "emulsifier free". Therefore, it has been difficult to achieve all the demands of high absorbability of ubiquinol into the body and the palatability of products.

CITATION LIST

Patent Literatures

Patent Document 1: Japanese Patent No. 3742602
Patent Document 2: Japanese Patent No. 5015548
Patent Document 3: Japanese Patent No. 5103188
Patent Document 4: Japanese Patent No. 3790530
Patent Document 5: Japanese Patent No. 3892881
Patent Document 6: International Publication WO 2007/148798
Patent Document 7: JP-A No. 2005-43
Patent Document 8: Japanese Patent No. 4361706
Patent Document 9: JP-T No. 2010-530904
Patent Document 10: Japanese Patent No. 2922017
Patent Document 11: Japanese Patent No. 5421674
Patent Document 12: International Publication WO 2003/62182

Non Patent Literature

Non-patent Document 1: Drug Delivery System, 25(4), 362-370, (2010)
Non-patent Document 2: Regul Toxicol Pharmacol., 47, 19-28, (2007)
Non-patent Document 3: Journal of American Geriatrics Society, 55(7), 1141-1142 (2007)

SUMMARY OF INVENTION

Technical Problem

It is an object of the present invention to provide a gel-like composition stably having a high content of ubiquinol. Specifically, it is the object of the present invention to provide a gel-like composition which has high absorbability of ubiquinol even when oils and fats and an emulsifier are not used and in which the ubiquinol is stably held even when the gel-like composition is stored over a long period of time and a method for efficiently producing the gel-like composition.

Solution to Problem

In order to achieve the object, the present inventors have repeatedly conducted an extensive research. As a result, the present inventors have found that, by dispersing the ubiquinol in a gel matrix containing gelatin and carbohydrate and/or water-soluble dietary fiber, a composition stably having a high content of ubiquinol can be obtained, and thus have accomplished the present invention.

More specifically, the present invention is as follows:

[1] A gel-like composition in which ubiquinol is dispersed and stabilized in a gel contains 0.2 to 15% by weight of ubiquinol, 5 to 15% by weight of gelatin, 55 to 80% by weight of carbohydrate and/or water-soluble dietary fiber, and 9 to 18% by weight of water, and further contains ascorbic acid and/or gallate type catechin,

[2] The gel-like composition according to [1] above contains 1 to 15% by weight of ubiquinol, 5 to 12% by weight of gelatin, 55 to 80% by weight of carbohydrate and/or water-soluble dietary fiber, 9 to 18% by weight of water, and 0.01 to 4% by weight of ascorbic acid and/or gallate type catechin,

[3] The gel-like composition according to [1] above contains 1 to 5% by weight of ubiquinol, 5 to 12% by weight of gelatin, 60 to 76% by weight of carbohydrate and/or water-soluble dietary fiber, and 13 to 18% by weight of water,

[4] The gel-like composition according to any one of [1] to [3] above further contains organic acid and flavor,

[5] The gel-like composition according to any one of [1] to [4] above, in which the content of an emulsifier and the content of oils and fats are less than 1% by weight,

[6] The gel-like composition according to any one of [1] to [5] above contains 0.1 to 2.0% by weight of pectin,

[7] The gel-like composition according to any one of [1] to [6] above, in which the ubiquinol is dispersed in a gel with an average particle diameter of 50 μm or less,

[8] The gel-like composition according to any one of [1] to [7] above, in which the weight ratio of ubiquinol/ubiquinone after allowed to stand at 37° C. in the air for 7 days is 99/1 or more,

[9] The gel-like composition according to any one of [1] to [8] above, in which the weight ratio of ubiquinol/ubiquinone after the gel-like composition is allowed to stand under an atmosphere of 40° C. and a humidity of 75% for 6 months is 95/5 or more,

[10] The gel-like composition according to any one of [1] to [9] above, in which the form of the gel-like composition is a gummy candy which is designed in such a manner that the weight of one piece is 1.0 to 4.0 g,

[11] A method for producing the gel-like composition according to [1] above at least containing ubiquinol, gelatin, carbohydrate and/or water-soluble dietary fiber, gelatin, and ascorbic acid and/or gallate type catechin includes (I) a process of heating and dissolving carbohydrate and/or water-soluble dietary fiber, and gelatin in water to prepare a dough, (II) a process of preparing a fluid liquid containing ubiquinol and gelatin and further containing ascorbic acid and/or gallate type catechin, and (III) a process of mixing the dough and the fluid liquid, and

[12] The method for producing a gel-like composition according to [11] above, includes a process of stirring and mixing ubiquinol melted at 46° C. or higher in the presence of at least gelatin, and pulverizing the ubiquinol until the average particle diameter of the ubiquinol reaches 50 μm or less.

Advantageous Effects of Invention

The gel-like composition of the present invention is a gel-like composition stably having a high content of ubiquinol, in which the long-term storage stability is high and high absorbability can be expected because the gel-like composition is a water dispersible gel. Therefore, the gel-like composition of the present invention is useful as a supplement.

Moreover, by processing the gel-like composition of the present invention into a predetermined shape, the gel-like composition is imparted with excellent portability as in former supplements and moreover the intake thereof becomes easier as compared with former supplements and a large amount of ubiquinol can be blended as necessary.

BRIEF DESCRIPTION OF THE DRAWINGS

FIG. 1 shows the transition of the ubiquinol concentration in blood obtained in Test example III-3. FIG. 1 shows changes in the ubiquinol concentration in blood by the intake of test foods based on a blood concentration before the intake of the test foods. The statistical analysis was conducted by one sample t-test and the significance level was set to 5% or less (P<0.05) on both sides. One in which the significant difference was obtained is indicated by "##".

FIG. 2 shows the area under the blood concentration—time curve (AUC) of the ubiquinol in blood obtained in Test Example III-3, which was calculated from the transition of the ubiquinol concentration in blood from 0 hour to 10 hours using a trapezoidal method. Higher values indicate that the absorbability is higher. The statistical analysis was conducted by one sample t-test and the significance level was set to 5% or less (P<0.05) on both sides.

FIG. 3 shows the area under the blood concentration—time curve (AUC) of the ubiquinol in blood obtained in Test Example III-3, which was calculated from the transition of the ubiquinol concentration in blood from 0 hour to 6 hours using a trapezoidal method. Higher values indicate that the absorption is higher. The statistical analysis was conducted by one sample t-test and the significance level was set to 5% or less (P<0.05) on both sides. One in which the significant difference was obtained is indicated by "#".

FIG. 4 shows the state of ubiquinol observed under an optical microscope of a product of the present invention obtained in Test Example III-3 and comparative products 1 and 2.

DESCRIPTION OF EMBODIMENTS

Hereinafter, the present invention is described in more detail.

A gel-like composition of the present invention is a gel composition in which ubiquinol is dispersed and stabilized in a gel and contains 0.2 to 15% by weight of ubiquinol, 5 to 15% by weight of gelatin, 55 to 80% by weight of carbohydrate and/or water-soluble dietary fiber, and 9 to 18% by weight of water, and further contains ascorbic acid and/or gallate type catechin.

In the present invention, the "gel" refers to a water-soluble organization containing gelatin, carbohydrate and/or water-soluble dietary fiber, and ascorbic acid and/or gallate type catechin and containing water as the solvent.

[(a) Ubiquinol]

The ubiquinol for use in the present invention is a functional component also referred to as a reduced coenzyme Q10, a reduced CoQ10, and a reduced form coenzyme Q10 and is an oil soluble solid substance. As the ubiquinol, commercially-available items may be used and those manufactured by Kaneka Corporation are mentioned. For example, "Kaneka QH" which is a purified product and "Kaneka QH stabilization powder (P30)" which is a prepared product manufactured by Kaneka Corporation and the like are mentioned and "Kaneka QH" is desirable in terms of cost and physical properties.

The content of the ubiquinol in the gel-like composition of the present invention is 0.2 to 15% by weight. When the content is less than 0.2% by weight, the effects peculiar to the ubiquinol excessively decrease. It is difficult that the content exceeds 15% by weight in terms of the stability of the ubiquinol or the physical properties of the gel. The content is preferably 1 to 14% by weight, more preferably 1 to 5% by weight, and still more preferably 1.8 to 4% by weight.

[(b) Gelatin]

The gelatin for use in the present invention is obtained by heating and modifying collagen which is protein mostly contained in the bone and the skin of animals. In the present invention, as the gelatin, any gelatin can be used without being particularly limited in the original living things (a pig, a cow, a fish, and the like) and the production methods (acid treatment, alkali treatment, and the like). The various kinds of gelatin may be used alone or as a mixture of two or more kinds thereof, irrespective of the original living things, the kind of treatment, the molecular weight, and the like.

The content of (b) the gelatin in the gel-like composition of the present invention is 5 to 15% by weight. When the content is less than 5% by weight, the gel strength of the gel-like composition is low and the shape retainability is poor. It is difficult that the content exceeds 15% by weight in terms of the production method. The content is preferably 5 to 12% by weight, more preferably 5 to 10% by weight, and still more preferably 6 to 10% by weight.

[(c) Carbohydrate and/or Water-Soluble Dietary Fiber]

As the carbohydrate for use in the present invention, sugar, starch syrup, glucose, high-fructose corn syrup, reduced maltose, reduced starch syrup, maltitol, sorbitol, xylitol, erythritol, trehalose, palatinose, reduced palatinose, and the like are mentioned, for example. As the water-soluble dietary fiber for use in the present invention, polysaccharides excluding polydextrose, hardly digestible dextrin, pectin, and the like are mentioned. As the polysaccharides, soybean polysaccharides, gum arabic, gellan gum, xanthan gum, tragacanth gum, guar gum, karaya gum, tamarind seed gum, ghatti gum, cassia gum, Locust bean gum, carrageenan, alginic acid, and the like are mentioned. In the present invention, the soybean polysaccharides and/or the gum arabic are particularly preferably used in terms of physical properties.

These carbohydrates and/or water-soluble dietary fibers are not particularly limited and may be used alone or as a mixture of two or more kinds thereof.

The content of (c) the carbohydrate and/or the water-soluble dietary fiber in the gel-like composition of the present invention is 55 to 80% by weight in total. When the content is in the range mentioned above, the physical properties of the gel can be maintained. The content is preferably 55 to 76% by weight and more preferably 60 to 76% by weight.

[(d) Water]

The content of (d) water in the gel-like composition of the present invention is 9 to 18% by weight. When the content is less than 9% by weight, the gel-like composition becomes excessively hard. The content exceeding 18% by weight is not preferable in terms of the storage stability of the gel-like composition. The content of the water is preferably 12 to 18% by weight and more preferably 13 to 18% by weight.

[(e) Ascorbic Acid and/or Gallate Type Catechin]

The gel-like composition of the present invention further contains ascorbic acid and/or gallate type catechin.

The ascorbic acid is also referred to as vitamin C and is used for foods as an antioxidant. The ascorbic acid for use in the present invention may also be one which is commercially available as a food additive. Salts of ascorbic acid may also be used and derivatives thereof may be acceptable. As the derivatives of ascorbic acid, "Asco Fresh" manufactured by Hayashibara Co., Ltd. and the like are mentioned, for example.

The gallate type catechin is one kind of catechins mostly contained in tea plant classified into genus *Camellia* such as green tea, black tea, or oolong tea, and is catechin having a galloyl group in the molecules such as ECg (epicatechin gallate), EGCg (epigallocatechin gallate), Cg (catechin gallate), and GCg (gallocatechin gallate). The catechins may be purified products or crude products or may be natural products containing these catechins or processed products thereof. Raw materials having a gallate type catechin proportion of 10% by weight or more are preferable in terms of flavor and the like.

The ascorbic acid and the gallate type catechin may be mixed for use.

In addition to the ascorbic acid and the gallate type catechin, water-soluble antioxidants such as catechin, other polyphenols, and α-lipoic acid, may be used in combination.

The total content of (e) the ascorbic acid and the gallate type catechin in the gel-like composition of the present invention may be the balance of the (a) to (d) above and is preferably 15% by weight or less.

In particular, the total content of the ascorbic acid and the gallate type catechin is preferably 0.01 to 4.0% by weight from the viewpoint of the balance between the taste and the physical properties of the gel-like composition.

The content of the ascorbic acid in the gel-like composition of the present invention is preferably 10% by weight or less, more preferably 0.1 to 4.0% by weight, and still more preferably 0.1 to 3.0% by weight from the viewpoint of the long-term storage stability and the shape retainability of the gel-like composition.

The content of the gallate type catechin in the gel-like composition of the present invention is preferably 2% by weight or less and more preferably 0.01 to 1.0% by weight in terms of the stability and the absorbability of ubiquinol.

[Arbitrary Components]

The gel-like composition of the present invention may contain arbitrary components such as organic acid, a flavor, a colorant, a sweetener, glycerol, fruit juice, dairy products, coffee, tea, plant extracts, a water-insoluble dietary fiber, a water-soluble antioxidant, and functional components other than ubiquinol as desired. By selecting these arbitrary components as appropriate to adjust the physical properties and the taste, a wide range of palatability can be given to the gel-like composition.

The arbitrary components mentioned above may be any component and are not particularly limited insofar as the component can be used for foods. The arbitrary components may be used in the range where the palatability and the physicochemical stability of the gel-like composition are not adversely affected.

In particular, it is preferable to blend the organic acid and the flavor in the gel-like composition in terms of palatability.

Examples of the organic acid include, for example, citric acid, malic acid, tartaric acid, lactic acid, acetic acid, adipic acid, and the like. Examples of the flavor include fruit flavors such as lemon flavor, orange flavor, grape flavor, and strawberry flavor, flavors of flowers such as a rose, flavors of herbs, flavors having the scent of tea, coffee, cola, soda, chocolate, vanilla, and dairy products, and the like.

Due to the fact that the gel-like composition of the present invention contains pectin, the long-term storage stability can be increased. The pectin is generally polysaccharide obtained from a dilute acid extract of citrus fruits or apple flesh and mainly contains a linear polymer of galacturonic acid in which a carboxyl group is partially methyl-esterified.

The content of the pectin in the gel-like composition of the present invention is preferably 0.1 to 2.0% by weight and more preferably 0.2 to 1.5% by weight.

From the viewpoint that the gel-like composition of the present invention also matches the taste and the physical properties and further the idea of consumers, particularly health-conscious consumers, the content of the emulsifier and the oils and fats each is preferably less than 1% by weight, more preferably less than 0.5% by weight, and still more preferably less than 0.1% by weight, and particularly preferably the emulsifier and the oils and fats are not contained.

The gel-like composition of the present invention is one in which ubiquinol is dispersed and stabilized in a gel. The "dispersed and stabilized" refers to a physicochemically stable state, e.g., a state in which ubiquinol is held without being modified into ubiquinone while the ubiquinol is being dispersed in the gel. The ubiquinone is an oxidized form of the ubiquinol and is also referred to as an oxidized coenzyme Q10 or simply referred to as a coenzyme Q10.

In the gel-like composition of the present invention, the average particle diameter of the ubiquinol dispersed in the gel containing gelatin, carbohydrate and/or water-soluble dietary fiber, ascorbic acid and/or gallate type catechin, and water is preferably adjusted to 50 μm or less from the viewpoint of increasing the absorbability into the body and the long-term storageability.

Due to the fact that the ubiquinol is dispersed with such a fine average particle diameter, the absorbability of the ubiquinol into the body can be improved and moreover the long-term storageability of the ubiquinol can also be improved.

The average particle diameter of the ubiquinol dispersed in the gel can be confirmed by observing the cross section of the gel under an optical microscope, observing the ubiquinol particles after dissolving the gel-like composition of the present invention in water under an optical microscope, or measuring the particles with a particle size distribution meter.

Moreover, the gel-like composition of the present invention is excellent in the storage stability of the ubiquinol. Specifically, the ubiquinol has features that, even when the gel-like composition of the present invention is irradiated with light for a long period of time as described in Examples described later, the ubiquinol is hardly converted to an oxidized type and is physicochemically in a very stable state.

For example, with respect to the storage stability of the gel-like composition of the present invention, the weight ratio of the ubiquinol/ubiquinone after the gel-like composition is allowed to stand at 37° C. in the air for 7 days is preferably 99/1 or more.

The storage stability can be measured according to a method described in the quantification of the ubiquinol of Examples described later.

In the gel-like composition in which the average particle diameter of the ubiquinol dispersed in the gel is adjusted to 50 μm or less as described above, the weight ratio of ubiquinol/ubiquinone after the gel-like composition is allowed to stand for 6 months under an atmosphere of 40° C. and a humidity of 75% is preferably 95/5 or more.

The storage stability can be measured according to the method described in the quantification of the ubiquinol of Examples described later.

The gel-like composition of the present invention is excellent in water dispersibility. When the gel-like composition is placed in about 40° C. water, and then stirred, for example, the gel is dissolved and the components in the gel are also uniformly dispersed to form a uniform suspension.

The ubiquinol is an oil-based component. Therefore, when the ubiquinol is mixed with water, and then allowed to stand still, the mixture is usually separated into the aqueous layer and the oil layer. However, when the gel-like composition of the present invention is dissolved in water, the mixture is not separated into the aqueous layer and the oil layer and the ubiquinol is dispersed in an emulsified state.

The gel-like composition of the present invention can be processed into various forms. As such processing, a gummy candy, the content in a capsule, a film shape, a sheet shape, a plate shape, a rod shape, and the like are mentioned.

As methods for the processing, known methods may be used. For example, when the gel-like composition of the present invention is processed into a gummy candy, a method including pouring the gel-like composition into a mold of a predetermined shape, and then solidifying the same is mentioned.

When the gel-like composition of the present invention is processed into the content in a capsule, a method including filling the gel-like composition into a capsule and a method including applying a dissolved material for capsule formation to the surface of the gel-like composition processed into a spherical shape of a desired size are mentioned.

When the gel-like composition of the present invention is processed into a film shape, a sheet shape, a plate shape, a rod shape, and the like, a method pouring the gel-like composition into a mold of a desired shape, and then solidifying the same and a method adjusting the shape with a rolling mill or the like are mentioned.

In particular, as the gel-like composition of the present invention, by adding organic acid and a flavor to the gel-like composition to prepare gummy candies in such a manner that the weight of one piece is 1.0 to 4.0 g, anyone from children to adults can deliciously take the gel-like composition every day.

In the present invention, the gummy candy refers to one having a form of a size which allows a consumer to hold the same with fingers and eat the same in one bite.

With respect to the weight of one piece, when the weight is less than 1.0 g, sufficient intake of the ubiquinol becomes difficult and when the weight exceeds 4.0 g, the size is excessively large, which makes it difficult for a consumer to eat the same, and thus the weights are not preferable.

[Production Method]

A method for producing the gel-like composition of the present invention having the above-described configuration includes a process of mixing ubiquinol, gelatin, carbohydrate and/or water-soluble dietary fiber, ascorbic acid and/or gallate type catechin, and water at 50° C. or higher, and then drying the solution to be obtained to obtain a gel-like composition.

A method for mixing ubiquinol, gelatin, carbohydrate and/or water-soluble dietary fiber, ascorbic acid and/or gallate type catechin, and water is not particularly limited. For example, carbohydrate and/or water-soluble dietary fiber and water are mixed and heated, an aqueous solution prepared by dissolving gelatin in heated water is added and mixed in the mixture, ubiquinol is added, and then the mixture is heated and mixed. The ascorbic acid and/or the gallate type catechin may be mixed at arbitrary timing. Subsequently, the obtained solution is poured into a mold (a starch mold, a silicone mold, and the like), and then dried to a desired moisture value, whereby a gel-like composition of a desired shape can be obtained.

The obtained gel-like compositions of various shapes may be taken out of the mold, and then the surface may be coated with a brightening agent or various kinds of saccharides.

As the brightening agent, plant wax such as carnauba wax, bees wax, shellac, paraffin wax, and the like are mentioned, for example. Vegetable oils and fats may be used. Examples of the saccharides include sugar, glucose, maltitol, sorbitol, xylitol, erythritol, trehalose, reduced palatinose, powder wafer, starch, and the like.

Moreover, as the mold, a starch mold with high dry efficiency is preferable. The starch mold refers to one obtained by spreading cornstarch powder in a shallow and flat container, removing the starch from the container and then forming dents.

In particular, in the gel-like composition of the present invention, from the viewpoint of efficiently preventing conversion of ubiquinol to ubiquinone and preventing the separation of ubiquinol in a dough, the following processes are preferably included:

(I) a process of heating and dissolving carbohydrate and gelatin in water to prepare a dough,
(II) a process of preparing a fluid liquid containing ubiquinol and gelatin and further containing ascorbic acid and/or gallate type catechin, and
(III) a process of mixing the gummy candy base and the fluid liquid. Hereinafter, each process is described.

[Process (I): Preparation of Dough]

This process is a process of preparing a dough containing carbohydrate and gelatin.

In the present invention, the type and the amount of the carbohydrate and the gelatin are not limited.

A method for preparing the dough may include heating and dissolving carbohydrate and gelatin in water according to a former method for producing a gummy candy. For example, a method including heating and dissolving carbohydrate, and then adding and mixing an aqueous gelatin solution prepared by dissolving gelatin with warm water to the dissolved carbohydrate to obtain a dough may be acceptable or a method including mixing all of carbohydrate and the same aqueous gelatin solution as above, and then heating and dissolving the mixture to obtain a dough may be acceptable. The order of adding the carbohydrate and the aqueous gelatin solution is not particularly limited.

The contents of the components in the dough are preferably adjusted to the following ranges from the viewpoint of the texture, the taste, the shape retainability, and the production adaptability of a gummy candy.

The content of the carbohydrate is preferably adjusted to 55 to 85% by weight.

The content of the gelatin is preferably adjusted to 5 to 15% by weight.

The water content is preferably adjusted to 10 to 30% by weight.

The dough may be liquid at least containing carbohydrate and gelatin and may contain, for example, various arbitrary components, such as a gelling agent, e.g., gum arabic or pectin, glycerol, minerals, amino acids, protein, dietary fibers, fruit juice, dairy products, an acidulant, a colorant, and a flavor.

The various arbitrary components for gummy candies may be components which can be generally used for gummy candies and the content of the components is not particularly limited.

[(II): Process of Preparing Fluid Liquid]

This process is a process of dissolving each component in water to prepare a fluid liquid.

Due to the fact that the fluid liquid contains ubiquinol and gelatin and further contains ascorbic acid and/or gallate type catechin, the ubiquinol is uniformly dispersed and, surprisingly, the gelling ability of the gelatin disappears, and fluidity is exhibited. Therefore, gummy candies can be continuously produced by the use of a quantitative supply device, such as a metering pump.

The gelatin is not particularly limited and may be the same as that for use in the dough or a gelatin different from that of the dough may be used.

The contents of the components in the fluid liquid are preferably adjusted to the following ranges from the viewpoint of the physical properties of the fluid liquid, the physical properties of gummy candies, and the stability of the ubiquinol.

The content of the ubiquinol is preferably adjusted to 1 to 30% by weight.

The content of the gelatin is preferably adjusted to 1 to 10% by weight.

The content of the ascorbic acid is preferably adjusted to 0 to 20% by weight.

The content of the gallate type catechin is preferably adjusted to 0 to 10% by weight.

The water content is preferably adjusted to 25 to 60% by weight.

The fluid liquid preferably further contains polysaccharides. Examples of the polysaccharides include soybean polysaccharides, gum arabic, pectin, gellan gum, xanthan gum, tragacanth gum, guar gum, karaya gum, tamarind seed gum, ghatti gum, cassia gum, Locust bean gum, carrageenan, alginic acid, and the like. In the present invention, it is particularly preferable to use soybean polysaccharides, gum arabic, pectin, and the like in terms of physical properties.

The fluid liquid may contain, in addition to the components mentioned above, arbitrary components such as carbohydrate, oils and fats, glycerol, alcohol, minerals, amino acids, protein, dietary fibers, fruit juice, dairy products, an acidulant, a colorant, and a flavor.

The various arbitrary components for a fluid liquid may be those which can be generally used for gummy candies and the content thereof is not particularly limited.

[Process (III): Mixing of Dough and Fluid Liquid]

This process is a process of mixing the dough obtained in the process (I) and the fluid liquid obtained in the process (II), respectively, to produce a gel-like composition.

The mixing method is not particularly limited insofar as the dough and the fluid liquid are uniformly mixed. Since the fluid liquid does not cause gelation at room temperature, the temperature particularly does not need to be controlled. However, the dough and the fluid liquid cause gelation at room temperature. Therefore, the mixing is preferably performed while keeping the mixture warm at 60° C. or higher.

With respect to the gel-like composition to be obtained in the process (III) above, the mixture is then filled into a mold, and then dried to a desired moisture value. Then, the resultant mixture is released from the mold, and then the surface is coated, whereby a gel-like composition is obtained.

The size and the material of the mold, the drying method, and the coating method may be those which are used for producing common gummy candies and are not particularly limited.

In particular, it is preferable in the production method of the present invention to stir and mix the ubiquinol melted at 46° C. or higher in the presence of at least gelatin and pulverize the ubiquinol until the average particle diameter of ubiquinol reaches 50 μm or less from the viewpoint of increasing the absorbability of the ubiquinol into the body.

As the stirring and mixing method in the pulverizing process described above, high-speed stirring by devices such as a homomixer and a homogenizer, stirring by a propeller depending on the property of the solution, and the like are mentioned but the method is not particularly limited insofar as particles of 50 μm or less are formed.

The mixing method of each component is not particularly limited insofar as the ubiquinol melted at 46° C. or higher may be stirred and mixed in the presence of at least gelatin until the average particle diameter reaches 50 μm or less for pulverization. A method including mixing carbohydrate and/or water-soluble dietary fiber and water and then heating, adding and mixing an aqueous solution prepared by dissolving gelatin in heated water, and then adding ubiquinol, melting the ubiquinol at 46° C. or higher, stirring and mixing the mixture until the average particle diameter of the ubiquinol reaches 50 μm or less, and then adding ascorbic acid and/or gallate type catechin and other arbitrary components, a method including mixing carbohydrate and/or water-soluble dietary fiber, ubiquinol, and water, heating the mixture to 46° C. or higher to melt the ubiquinol, adding and mixing an aqueous solution prepared by dissolving gelatin in heated water, and then adding ascorbic acid and/or gallate type catechin and other arbitrary components to the mixture, a method including adding ubiquinol to an aqueous solution containing gelatin, stirring and mixing the mixture at 46° C. or higher to pulverize the ubiquinol until the average particle diameter reaches 50 μm or less, and then adding and mixing the resultant solution in an aqueous solution containing gelatin, carbohydrate and/or water-soluble dietary fiber, ascorbic acid and/or gallate type catechin, water, and other arbitrary components, and the like are mentioned.

In the present invention, ubiquinol does not melt and does not disperse with an average particle diameter of 50 μm or less at less than 46° C.

Then, the obtained solution is molded into a desired form, and then, after passing through processes such as drying as necessary, a gel-like composition is obtained. The molding method is not particularly limited and a method including pouring the solution into a mold (a starch mold, a silicone mold, and the like), a method including molding the solution into a sheet shape with a sheet molding machine, a method including molding the solution with a soft capsule filler, and the like are mentioned, for example.

With respect to the obtained gel-like compositions of various shapes, the surface may be coated with a brightening agent or various kinds of saccharides.

As the brightening agent, plant wax such as carnauba wax, bees wax, shellac, paraffin wax, and the like are mentioned, for example. As the brightening agent, plant oils and fats may be used. As the saccharides, sugar, glucose, maltitol, sorbitol, xylitol, erythritol, trehalose, reduced palatinose, powder wafer, starch, and the like are mentioned. When oils and fats are used for the coating of the gel-like composition of the present invention, the oils and fats used for the coating are not contained in the content.

The gel-like composition of the present invention can be obtained as described above. The gel-like composition of the present invention is suitable as a supplement which is easily taken without water and can be easily taken by anyone at any place. Furthermore, due to the fact that the ubiquinol is dispersed in the gel containing gelatin, carbohydrate and/or water-soluble dietary fiber, ascorbic acid and/or gallate type catechin, and water, the dispersibility in water is substantially high, and thus high absorbability in the body is expected.

As a major factor for which consumers cannot continue the intake of commercially available supplements every day, troublesomeness of the intake or forgetting to take is mentioned, for example. The gel-like composition of the present invention can give high palatability and allows consumers to deliciously take nutritional components, which are greatly advantageous for consumers to pleasantly continue the intake every day.

For example, by preparing the gel-like composition of the present invention into gummy candies in such a manner that the weight of one piece is 1.0 to 4.0 g by adding organic acid and a flavor, the gel-like composition is imparted with a shape which is familiar to anyone from children to adults for eating and does not give uncomfortable feeling and further the gel-like composition can be deliciously taken every day.

In the present invention, the gummy candy refers to one having a form of a size which allows a consumer to hold the same with fingers and eat the same in one bite.

The weight of one piece is preferably 0.3 to 5.0 g and more preferably 1.0 to 4.0 g from the viewpoint of the balance between the intake amount of ubiquinol and the ease of intake.

EXAMPLES

Hereinafter, the present invention is specifically described with reference to Examples but the present invention is not limited to Examples at all. In the following description of Examples, "%" and "part(s)" are based on weight.

Reference Example I-1

Sugar, starch syrup (manufactured by Nihon Cornstarch Corporation, "Koso Syrup R75" (Solid content of 75% by weight, which similarly applies in the following description), and water were mixed, the mixture was heated to 100° C., an aqueous gelatin solution prepared by dissolving gelatin (manufactured by Nitta Gelatin, Inc., "APH-250") in 50° C. water (in an amount 1.4 times the amount of gelatin) was added to the mixture, and then ubiquinol (manufactured by Kaneka Corporation, "Kaneka QH", which similarly applies in the following description), citric acid, and lemon flavor were added, followed by stirring and mixing. The obtained solution was kept warm at 70° C., filled into a starch mold stamped into a hemispherical shape of 20 mm in diameter, and then dried at 40° C. until the moisture value reached 16% by weight. Thereafter, the starch was removed, and then a brightening agent (carnauba wax) was thinly applied to the surface, whereby hemispherical gel-like compositions were obtained in such a manner that the weight of one piece was 2.5 g. The amount of the components blended in the gel-like composition and the ratio thereof are shown in Table 1 (The same applies in Examples I-1 to I-6 and Comparative Examples I-1 to I-5 described later.)

The obtained gel-like composition was a health supplement which allows the intake of ubiquinol, whose amount is as large as 50 mg, with one piece and also allows easy intake in one bite without water and delicious intake of ubiquinol. However, the weight ratio of ubiquinol and ubiquinoline was lower than that in Examples I-1 to I-5 described later.

Examples I-1 to I-5, Comparative Example I-1

Sugar, starch syrup, and water were mixed, the mixture was heated to 100° C., an aqueous gelatin solution prepared by dissolving gelatin in 50° C. water (in an amount 1.4 times the amount of gelatin) was added to the mixture, and then ubiquinol, ascorbic acid, and lemon flavor were added, followed by stirring and mixing. The obtained solution was filled into a starch mold stamped into a hemispherical shape of 16 mm in diameter, and then dried to a desired moisture value. Thereafter, the starch was removed, and then a brightening agent (carnauba wax) was thinly applied to the surface, whereby hemispherical gel-like compositions were obtained in such a manner that the weight of one piece was 1 g.

The gel-like compositions obtained in Examples I-1 to I-5 were health supplements which allow the intake of ubiquinol, whose amount is as large as 20 mg, with one piece and also allows easy intake in one bite without water and delicious intake of ubiquinol.

On the other hand, in the gel-like composition obtained in Comparative Example I-1, the carbohydrate content was large but the gelatin content was small, and therefore the shape retainability was low and the compositions adhere to each other, so that the gel-like composition was not suitable as a supplement.

Comparative Example I-2

Gel-like compositions were produced in the same manner as in Example I-1 except changing the gelatin of Example I-1 to collagen peptide (manufactured by Nitta Gelatin, Inc., "SCP-5200").

Comparative Example I-3

Agar was mixed with a small amount of sugar, water in amount 10 times the amount thereof was added, the mixture was heated to 100° C., sugar and starch syrup were added, and then the mixture was further heated. When the solution was heated until the moisture value of the solution reached 17% by weight, ubiquinol, ascorbic acid, and lemon flavor were added, the mixture was stirred and mixed, the resultant mixture was filled into a silicone mold, and then the silicone mold was cooled, whereby gel-like compositions were produced.

Example I-6

Maltitol (manufactured by Roquette, "Sweet Pearl" (Registered Trademark) P200) and polydextrose (manufactured by Danisco, "Litesse Ultra", were mixed, water was added, the mixture was heated to 100° C., an aqueous solution prepared by dissolving gelatin and collagen peptide in 50° C. water (in an amount 1.2 times the total amount of gelatin and collagen peptide) was added to the mixture, ubiquinol, ascorbic acid, lemon flavor were added, and then the mixture was stirred and mixed. The obtained solution was filled into a starch mold stamped into a hemispherical shape of 20 mm in diameter, and then dried until the moisture value reached 15.5%. Thereafter, the starch was removed, and then a brightening agent (carnauba wax) was thinly applied to the surface, whereby hemispherical gel-like compositions were obtained in such a manner that the weight of one piece was 2.5 g.

The obtained gel-like composition was a health supplement which allows the intake of ubiquinol, whose amount is as large as 100 mg, with one piece and also allows easy intake in one bite without water and delicious intake of ubiquinol.

Comparative Example I-4

50 parts of sugar and 48 parts of enzyme starch syrup were mixed and dissolved, and then concentrated in a vacuum pan under the conditions of −550 mmHg and 115° C. until the moisture value reached 3.0% by weight. Thereafter, 7 parts of powder gelatin (manufactured by Nitta Gelatin, Inc., "G fine powder"), 2 parts of ubiquinol, 1.5 parts of citric acid, and 0.2 parts of lemon flavor were added and mixed, and then molded into a size in such a manner that the weight of one piece was 2.5 g, whereby candy-like compositions were obtained.

Comparative Example I-5

Water was sprayed to powder sugar using a fluidized bed granulator for granulation. To 88 parts of the obtained sugar granulated product, 7 parts of powder gelatin, 1.5 parts of citric acid, 2 parts of ubiquinol, and 0.2 parts of powder lemon flavor were added and mixed, and then prepared into tablet-like compositions having such a size that the weight of one piece was 2.5 g using a rotary type tableting machine.

Test Example I-1

Quantification of Ubiquinol

The various compositions obtained in Reference Example I-1, Examples I-1 to I-6, and Comparative Examples I-2 to I-5 were arranged in a tray, allowed to stand under a 37° C. atmosphere for 7 days under the irradiation with 500 lux light, and then the remaining amount of the ubiquinol was quantified according to the following analysis method. The results are shown in Table 1.

In Table 1, the "weight ratio of ubiquinol/ubiquinone" shows the ratio in the various compositions after the passage of 7 days after the production thereof.

The "ubiquinol remaining ratio" refers to the amount of the ubiquinol remaining in the various compositions after the passage of 7 days after the production to the amount of the added ubiquinol.

<Analysis Method>

1 g of each of the various compositions was finely pulverized, 5 mL of water was added, the mixture was warmed and dissolved at 50° C. for 10 minutes, 5 mL of saturated salt solution, 20 mL of ethanol, and 20 mL of hexane were added, the mixture was shaken with a centrifugal separator at 280 rpm for 5 minutes, the resultant mixture was allowed to stand still to be separated into two layers, 2 mL of the hexane layer was extracted with a volumetric pipette, diluted to 10 ml with methanol in a measuring flask, and then the HPLC analysis was conducted. The conditions of the HPLC analysis are as follows.

<HPLC Analysis Conditions>

Column: Reversed phase column "Unison US-C8" (2.0 mmi.d.×150 mm, manufactured by Imtakt Corporation)
Mobile phase: A . . . $H_2O$ (0.1% trifluoroacetic acid (TFA)), B . . . Acetonitrile (0.1% TFA)
Flow rate: 0.5 mL/min
Pouring: 10 μL
Detection: 290 nm (Reduced CoQ10), 275 nm (Oxidized CoQ10)
Gradient (% by volume): from 5% A/95% B to 0% A/100% B over 5 minutes, for 5 minutes at 100% B (all linear line)

TABLE 1

| | | Reference Example I-1 | Example I-1 | Example I-2 | Example I-3 | Example I-4 | Example I-5 | Example I-6 |
|---|---|---|---|---|---|---|---|---|
| Formula (part by weight) | Sugar | 45 | 45 | 45 | 45 | 45 | 45 | |
| | Starch syrup | 40 | 40 | 40 | 40 | 40 | 40 | |
| | Maltitol | | | | | | | 30 |
| | Polydextrose | | | | | | | 32 |
| | Gelatin | 7.0 | 7.0 | 7.0 | 7.0 | 10 | 5.0 | 9.0 |
| | Collagen peptide | | | | | | | 7.0 |
| | Agar | | | | | | | |
| | Citric acid | 1.5 | | | | | | |
| | Ascorbic acid | | 2.0 | 2.0 | 2.0 | 2.0 | 2.0 | 3.0 |
| | Ubiquinol | 2.0 | 2.0 | 2.0 | 2.0 | 2.0 | 2.0 | 4.0 |
| | Lemon flavor | 0.2 | 0.2 | 0.2 | 0.2 | 0.2 | 0.2 | 0.2 |
| Proportion in composition (% by weight) | Carbohydrate and/or water-soluble dietary fiber | 73.5 | 73.1 | 74.4 | 71.3 | 70.6 | 74.8 | 61.5 |
| | Gelatin | 6.9 | 6.8 | 6.9 | 6.7 | 9.4 | 5.0 | 8.9 |
| | Ubiquinol | 2.0 | 1.9 | 2.0 | 1.9 | 1.9 | 2.0 | 4.0 |
| | Other components | 1.7 | 2.1 | 2.2 | 2.1 | 2.1 | 2.2 | 10.1 |
| | Water content | 16.0 | 16.0 | 14.5 | 18.0 | 16.0 | 16.0 | 15.5 |

TABLE 1-continued

|  |  |  |  |  |  |  |  |
|---|---|---|---|---|---|---|---|
| Total | 100.0 | 100.0 | 100.0 | 100.0 | 100.0 | 100.0 | 100.0 |
| Weight ratio of Ubiquinol/Ubiquinone | 99.3/0.7 | 99.7/0.3 | 99.7/0.3 | 99.7/0.3 | 99.5/0.5 | 99.7/0.3 | 99.5/0.5 |
| Ubiquinol remaining ratio (%) | 100.0 | 100.0 | 100.0 | 100.0 | 99.5 | 100.0 | 100.0 |

|  |  | Comparative Example I-1 | Comparative Example I-2 | Comparative Example I-3 | Comparative Example I-4 | Comparative Example I-5 |
|---|---|---|---|---|---|---|
| Formula (part by weight) | Sugar | 45 | 45 | 48 | 50 | 88 |
|  | Starch syrup | 40 | 40 | 40 | 48 |  |
|  | Maltitol |  |  |  |  |  |
|  | Polydextrose |  |  |  |  |  |
|  | Gelatin | 3.0 |  |  | 7.0 | 7.0 |
|  | Collagen peptide |  | 7.0 |  |  |  |
|  | Agar |  |  | 4.0 |  |  |
|  | Citric acid |  |  |  | 1.5 | 1.5 |
|  | Ascorbic acid | 2.0 | 2.0 | 2.0 |  |  |
|  | Ubiquinol | 2.0 | 2.0 | 2.0 | 2.0 | 2.0 |
|  | Lemon flavor | 0.2 | 0.2 | 0.2 | 0.2 | 0.2 |
| Proportion in composition (% by weight) | Carbohydrate and/or water-soluble dietary fiber | 76.6 | 73.1 | 76.0 | 86.3 | 88.3 |
|  | Gelatin | 3.1 | 0.0 | 0.0 | 7.0 | 7.0 |
|  | Ubiquinol | 2.0 | 1.9 | 1.9 | 2.0 | 2.0 |
|  | Other components | 2.2 | 9.0 | 6.0 | 1.7 | 1.7 |
|  | Water content | 16.0 | 16.0 | 16.0 | 3.0 | 1.0 |
| Total |  | 100.0 | 100.0 | 100.0 | 100.0 | 100.0 |
| Weight ratio of Ubiquinol/Ubiquinone |  | — | 98.9/1.1 | 97.8/2.2 | 98.1/1.9 | 73.0/27.0 |
| Ubiquinol remaining ratio (%) |  | — | 98.8 | 83.5 | 93.0 | 69.7 |

It can be said from the results shown in Table 1 that the gel-like compositions obtained in Examples I-1 to I-6 are excellent in the stability of the ubiquinol because the weight ratio of ubiquinol/ubiquinone is 99.5/0.5 or more and the ubiquinol remaining ratio is also 99.5% or more, which were very high numerical values.

On the other hand, it is found that the various compositions obtained in Comparative Example I-2 to I-5 are inferior in the stability of the ubiquinol to the gel-like compositions obtained in Examples I-1 to I-6 because the weight ratio of ubiquinol/ubiquinone is less than 99/1 and the ubiquinol remaining ratio is also less than 99%. In the gel-like composition obtained in Comparative Example I-2, the ubiquinol remaining ratio is relatively high but is lower than that of the gel-like compositions obtained in Examples I-1 to I-6 and the shape retainability is insufficient and sticking to the teeth occurs, and therefore the gel-like composition obtained in Comparative Examples I-2 is not suitable for eating.

Example I-7

30 parts of sugar, 30 parts of high-fructose corn syrup (manufactured by Nihon Cornstarch Corporation, "HIGH FRACT M" (Bx. 75)), 18 parts of palatinose (manufactured by Mitsui Sugar Co., Ltd., "Palatinose (Registered Trademark) IC"), and 0.6 parts of pectin (manufactured by GENU, "AS Confectionery") were mixed, water was added to the mixture, the mixture was heated to 100° C., an aqueous gelatin solution prepared by dissolving 7.9 parts of gelatin in 11 parts of 50° C. water was added to the mixture, 1.8 parts of ubiquinol, 1.8 parts of ascorbic acid, and 0.2 parts of lemon flavor were added to the mixture, and then the mixture was stirred and mixed. The obtained solution was filled into a starch mold stamped into a columnar shape of 16 mm in diameter, and then dried until the moisture value reached 16%. Thereafter, the starch was removed, and then a brightening agent (carnauba wax) was thinly applied to the surface, whereby hemispherical gel-like compositions were obtained in such a manner that the weight of one piece was 2 g. The content of each component in the gel-like composition is as follows: 1.8% by weight of ubiquinol, 8.0% by weight of gelatin, 71.5% by weight of carbohydrate, 16.0% by weight of water, and 2.7% by weight of other components.

The obtained gel-like composition was a health supplement which allows the intake of ubiquinol, whose amount is as large as 36 mg, with one piece and also allows easy intake in one bite without water and delicious intake of ubiquinol.

Test Example I-2

Long-Term Storage Test

The gel-like composition obtained in Example I-7 was filled into a polyethylene container, and then sealed. Thereafter, the container was stored for 3 months in a thermostat of 40° C. and a humidity of 75%. Thereafter, the ubiquinol remaining amount was quantified in the same manner as in the analysis method described above. The results were as follows: the weight ratio of ubiquinol/ubiquinone was 99.3/0.7 and the ubiquinol remaining ratio was 98.3%.

Therefore, it is found that the gel-like composition obtained in Example I-7 is excellent in long-term storageability of ubiquinol.

Test Example I-3

Water Dispersibility Test

One piece of each of the various compositions obtained in Example I-1 and Comparative Examples I-4 and I-5 was placed in a 100 mL beaker, 50 mL of 42° C. water was poured into each beaker, and then the mixture was stirred for 15 minutes with a magnetic stirrer while being kept warm at 42° C. Then, the stirring was stopped, and then the mixture was allowed to cool to room temperature. The gel-like composition of Example I-1 dissolved and the ubiquinol was not separated, so that a uniform aqueous solution was obtained. However, both the various compositions obtained in Comparative Examples I-4 and I-5 dissolved but the ubiquinol was separated, so that a yellow lump was floating on the water surface.

Therefore, it is found that the ubiquinol in the gel-like composition obtained in Example I-1 has high dispersibility in water, which suggests that high oral absorbability is achieved.

Test Example I-4

Observation of Particles

When ubiquinol powder (Kaneka QH) was observed under an optical microscope ("BX41", manufactured by Olympus, Inc.) at a magnification of 400 times, the powder had an irregular crystal structure. On the other hand, when the composition of Example I-7 was similarly observed, crystals were not observed at all. The results show that, in the gel-like composition of the present invention, the ubiquinol is dispersed in a fine particle state, and thus it is greatly expected that the absorbability is higher than in the case of taking the same in a coarse crystal state.

Example II-1

40 parts of sugar, 50 parts of enzyme starch syrup (Bx. 75), 0.3 parts of pectin, and 12 parts of water were mixed, and then heated and concentrated at 102° C. for 5 minutes until the total amount reached 97 parts to prepare a syrup. Then, 6 parts of gelatin melted in 8 parts of 60° C. warm water beforehand was mixed with the prepared syrup to prepare 111 parts of a gummy candy base. The obtained gummy candy base was kept warm at 70° C.

Separately, 1 part of gelatin and 0.5 parts of gum arabic were mixed in 3 parts of water and dissolved under heating, an aqueous solution in which 0.3 parts of green tea extract (Trade name: Sunphenon 90S, Gallate type catechin content of 65% by weight, manufactured by Taiyo Kagaku Co., Ltd., which similarly applies in the following description) was dissolved in 1.1 parts of water was added and mixed in the mixture while warming, and then 0.1 parts of citric acid, 2 parts of ascorbic acid, 0.83 parts of ubiquinol (manufactured by Kaneka Corporation, Ubiquinol/Ubiquinone=98/2, which similarly applies in the following description), 1 part of grape juice, and 0.17 parts of grape flavor were added and mixed to prepare 10 parts of fluid liquid. The obtained fluid liquid was placed under room temperature.

A gummy candy liquid obtained by mixing 111 parts of the gummy candy base and 10 parts of the fluid liquid prepared above was filled into a starch mold in which hemispherical dents of 15 mm in diameter were formed while keeping the gummy candy liquid warm at 70° C. Then, the resultant substance was dried at 40° C. for 48 hours, and then taken out of the starch mold. Then, a brightening agent was applied to the surface for coating, whereby gummy candies having a unit weight of 3 g and a moisture value of 16% were produced.

Example II-2

Gummy candies were produced in the same manner as in Example II-1 except removing the gum arabic and the green tea extract from Example II-1.

Comparative Example II-1

40 parts of sugar, 50 parts of enzyme starch syrup, 0.3 parts of pectin, 0.83 parts of ubiquinol, and 12 parts of water were mixed, and then heated and concentrated at 102° C. for 5 minutes until the total amount reached 97.83 parts to prepare a syrup. Then, 6 parts of gelatin melted in 8 parts of 60° C. warm water beforehand was mixed with the prepared syrup to prepare 111.83 parts of a gummy candy base. The obtained gummy candy base was kept warm at 70° C.

Separately, 1 part of gelatin and 0.5 parts of gum arabic were mixed with 3 parts of water and dissolved under heating, an aqueous solution in which 0.3 parts of green tea extract was dissolved in 1.1 parts of water was added and mixed in the mixture while warming, and then 0.1 parts of citric acid, 2 parts of ascorbic acid, 1 part of grape juice, and 0.17 parts of grape flavor were added and mixed to prepare 9.17 parts of fluid liquid. The obtained fluid liquid was placed under room temperature.

111.83 parts of the gummy candy base and 9.17 parts of the fluid liquid prepared above were mixed, and then gummy candies were produced in the same manner as in Example II-1.

Test Example II-1

Stability Test of Ubiquinol in Gummy Candy

In order to investigate the stability of the ubiquinol in the gummy candies obtained in Examples II-1 and II-2 and Comparative Example II-1, the content of the ubiquinol and the ubiquinone in the gummy candies under the following three conditions were quantified by the same analysis method as that of Test Example I-1. The weight ratio of the quantified ubiquinol/ubiquinone is shown in Table 2.
(1) Immediately after production
(2) After the passage of 30 days in an environment of 37° C./Humidity 85% after placing the gummy candies in a light blocking plastic bag
(3) After the passage of 30 days in an environment of 25° C./Humidity 50% after placing the gummy candies in a transparent plastic bag

TABLE 2

| | Conditions | Reduced type/ Oxidized type 1) |
|---|---|---|
| Example II-1 | (1) Immediately after production | 97.7/2.3 |
| | (2) 37° C./Humidity 85% | 97.0/3.0 |
| | (3) Light irradiation | 97.4/2.6 |
| Example II-2 | (1) Immediately after production | 97.8/2.2 |
| | (2) 37° C./Humidity 85% | 97.6/2.4 |
| | (3) Light irradiation | 97.2/2.8 |
| Comparative Example II-1 | (1) Immediately after production | 93.1/6.9 |

1) Ubiquinol/Ubiquinone (weight ratio)

The results of Table 2 show that, even when the gummy candies obtained in Examples II-1 and II-2 were exposed to the conditions where the ubiquinol likely becomes unstable, e.g., in the case where the gummy candies were exposed to heat of 60° C. or higher and oxygen (Condition (1)), in the case where the gummy candies were exposed to a medium temperature and high humidity (Condition (2)), and in the case where the gummy candies were irradiated with light (Condition (3)), the ubiquinol in the gummy candies is maintained at a ratio as high as 97% or higher, and therefore the ubiquinol is held in a physicochemically stable state. Moreover, it can be said from this fact that the ubiquinol is hard to be converted to an oxidized type even in the fluid liquid, and thus the ubiquinol is physicochemically stable.

On the other hand, in Comparative Example II-1, it is found that, due to the exposure to heat and oxygen in the production process, the retention of the ubiquinol is 93.1/6.9, which is lower than that of Example II-1, even immediately after the production. Herein, the gummy candy base is generally exposed to heat or oxygen for a longer period of time in an actual production site, and thus it is anticipated that the retention of the ubiquinol in the gummy candies to be obtained becomes still lower.

Comparative Example II-2

0.5 parts of gum arabic and 3 parts of water were mixed and heated, an aqueous solution in which 0.3 parts of green tea extract was dissolved in 1.1 parts of water was added and mixed in the mixture while warming, and then 0.1 parts of citric acid, 2 parts of ascorbic acid, 0.83 parts of ubiquinol, 1 part of grape juice, and 0.17 parts of grape flavor were added and mixed to prepare a fluid liquid. In the obtained fluid liquid, the ubiquinol was immediately separated.

Comparative Example II-3

1 part of gelatin, 0.5 parts of gum arabic, and 4.1 parts of water were mixed and heated, and then 0.1 parts of citric acid, 0.83 parts of ubiquinol, 1 part of grape juice, and 0.17 parts of grape flavor were added and mixed in the mixture while warming, but the obtained mixture was solidified at room temperature.

The results of Example II-1 and Comparative Examples II-2 and II-3 show that gelatin is required and ascorbic acid or gallate type catechin is required in order to obtain a fluid liquid which shows fluidity at room temperature and in which ubiquinol is uniformly dispersed.

Example II-3

60 parts of sugar, 40 parts of high-fructose corn syrup (Bx. 75), and 12 parts of water were mixed, 10 parts of gelatin melted in 15 parts of 60° C. warm water beforehand was mixed, and then the mixture was heated and concentrated at 102° C. for 5 minutes until the total amount reached 129 parts to prepare a gummy candy base. The obtained gummy candy base was kept warm at 70° C.

Separately, 2 parts of gelatin and 2.4 parts of gum arabic were mixed with 6.3 parts of water and dissolved under heating, an aqueous solution in which 0.6 parts of EGCg (Trade name: Sunphenon EGCg, Gallate type catechin content of 95% or more, manufactured by Taiyo Kagaku Co., Ltd.) was dissolved in 2 parts of water was added and mixed while warming, and then 1.2 parts of citric acid, 0.3 parts of ubiquinol, 1 part of grape juice, and 0.2 parts of grape flavor were added and mixed to prepare 16 parts of fluid liquid. The obtained fluid liquid was placed under room temperature.

A gummy candy liquid obtained by mixing 129 parts of the gummy candy base and 16 parts of the fluid liquid prepared above was filled into a starch mold in which hemispherical dents of 15 mm in diameter were formed while keeping the gummy candy liquid warm at 70° C. Then, the resultant substance was dried at 40° C. for 48 hours, and then taken out of the starch mold. Then, a brightening agent was applied to the surface for coating, whereby gummy candies having a unit weight of 3 g and a moisture value of 16% were produced. The obtained gummy candies were placed in a light blocking plastic bag. After the passage of 30 days in an environment of 37° C./Humidity 85%, the weight ratio of ubiquinol/ubiquinone was measured in the same manner as in Test Example II-1. The results are shown in Table 3.

Example II-4

50 parts of sugar, 30 parts of enzyme starch syrup, 0.4 parts of pectin, and 13 parts of water were mixed, and then heated and concentrated at 102° C. for 5 minutes until the total amount reached 88 parts to prepare a syrup. Then, 7 parts of gelatin melted in 9 parts of 60° C. warm water beforehand was mixed with the syrup to prepare 104 parts of a gummy candy base. The obtained gummy candy base was kept warm at 70° C.

Separately, 0.5 parts of gelatin and 0.3 parts of soybean polysaccharides were mixed with 3 parts of water and dissolved under heating, a solution in which 0.35 parts of green tea extract was dissolved in 2.15 parts of water and 2 parts of ethanol was added and mixed in the mixture while warming, and then 2 parts of ascorbic acid, 1.5 parts of ubiquinol, 1 part of grape juice, and 0.2 parts of grape flavor were added and mixed to prepare 13 parts of fluid liquid. The obtained fluid liquid was placed under room temperature.

The gummy candy base and the fluid liquid prepared above each were quantitatively supplied to a preparation tank using a metering pump in such a manner as to have [Flow rate (kg/min) of gummy candy base:Flow rate (kg/min) of fluid liquid=104:13] and mixed, and then a gummy candy liquid was filled into a starch mold in which hemispherical dents of 15 mm in diameter were formed in a state where the liquid was warmed to 70° C. Then, the resultant substance was dried at 40° C. for 48 hours, and then taken out of the starch mold. Then, a brightening agent was applied to the surface for coating, whereby gummy candies having a unit weight of 2.0 g and a moisture value of 16% were produced. The weight ratio of ubiquinol/ubiquinone in the obtained gummy candies was determined in the same manner as in Test Example 1 and is shown in Table 3.

TABLE 3

| | Reduced type/<br>Oxidized type 1) |
|---|---|
| Example II-3 | 97.0/3.0 |
| Example II-4 | 97.4/2.6 |

The results of Table 3 show that the ubiquinol in all the gummy candies of Examples II-3 and II-4 is maintained at a ratio as high as 97% or higher, and therefore the ubiquinol is held in a physicochemically stable state. When the ratio of ubiquinol/ubiquinone of the raw materials to be used is high, it is natural that the ratio of the ubiquinol/ubiquinone in the gummy candies becomes high corresponding to the ratio.

Example III-1

Sugar, starch syrup (manufactured by Nihon Cornstarch Corporation, "Koso Syrup R75" (Solid content of 75% by weight), Pectin (manufactured by GENU, "GENUpectin type 121-J slow set"), and water were mixed, the mixture was heated to 100° C., and then an aqueous gelatin solution prepared by dissolving gelatin (manufactured by Nitta Gelatin, Inc., "APH-250") in 50° C. water (in an amount 1.4 times the amount of gelatin) was added and mixed in the mixture. The obtained substance is used as a gummy candy base. Separately, a solution produced by mixing ubiquinol (manufactured by Kaneka Corporation, "Kaneka QH", which similarly applies in the following description), ascorbic acid, a green tea extract (manufactured by Taiyo Kagaku Co., Ltd., "Sunphenon 90S", gallate type catechin content of 65% by weight), mango flavor, orange juice, glycerol, carotenoid pigment, and a soybean dietary fiber at 70° C. was mixed with the gummy candy base, the mixture was kept warm at 70° C., the resultant mixture was filled into a starch mold stamped into a columnar shape of 20 mm in diameter, and then the mixture was dried at 40° C. until the moisture value reached 16% by weight. Thereafter, the starch was removed, and then a brightening agent (carnauba wax) was thinly applied to the surface, whereby cylindrical gummy candy-like products were obtained in such a manner that the weight of one piece was 2.5 g.

The formulation of each component was as follows: ubiquinol: 2.0% by weight, gelatin: 6.9% by weight, carbohydrate and/or water-soluble dietary fiber: 69% by weight (sugar: 40% by weight, starch syrup: 29% by weight (as solid content)), water-soluble antioxidant: 2.2% by weight (ascorbic acid: 2.0% by weight, gallate type catechin: 0.2% by weight), pectin: 0.8% by weight, water: 16% by weight, other components: 3.1% by weight.

The obtained gummy candy product was a health supplement which allows the intake of ubiquinol, whose amount is as large as 50 mg, with one piece and also allows easy intake in one bite without water and delicious intake of ubiquinol.

Test Example III-1

Measurement of Average Particle Diameter of Ubiquinol

The gummy candy products obtained in Example III-1 were dissolved in 50° C. water in an amount 30 times the amount of the gummy candy products, and then the particle diameter of the ubiquinol was measured with a particle size distribution meter (manufactured by Beckman Coulter). Then, the average particle diameter was 11 µm and a peak of 50 µm or more was not detected. When the solution was observed (magnification of 400 times) under an optical microscope (manufactured by Olympus, Inc.), all the particles had a particle diameter of 50 µm or less. The particles were dyed red with an oil red, and therefore it was able to be confirmed that the particles were ubiquinol particles.

Test Example III-2

Stability Test of Ubiquinol in Gummy Candy

The gummy candy products obtained in Example III-1 were subjected to a 6 month storage test under an atmosphere of 40° C. and humidity of 75% in the following styles.
(A) The gummy candy products were filled into a plastic container to fill commercially-available gummy candies, and then the container was covered.
(B) The gummy candy products were filled into a plastic bag to fill commercially-available gummy candies, and then the container was sealed with a heat seal.

When the weight ratio of the ubiquinol/ubiquinone after the test was measured by the same analysis method as that of Test Example I-1, (A) 98.5/1.5 and (B) 99.4/0.6 were obtained. Therefore, it was found that, even when the gummy candy product was commercialized and stored at a high temperature for a long period of time in the same manner as in former gummy candies, the oxidation of the ubiquinol to ubiquinone is prevented and notably outstanding storage stability of the ubiquinol is exhibited.

Test Example III-3

Absorbability Test in Humans (Verification Test of Blood Component by Intake of Ubiquinol)

(1) Preparation of Test Sample
(1-1) Ubiquinol Containing Gummy Candy (Product of the Present Invention)

The gummy candy product obtained in Example III-1 was used as a product of the present invention. The product of the present invention allowed the intake of 100 mg of ubiquinol with two pieces (5 g).
(1-2) Ubiquinol Containing Capsule As a ubiquinol containing capsule (comparative product 1), a capsule containing 33.3% by weight of ubiquinol was prepared. Safflower oil and ubiquinol were mixed as raw materials, and then the mixture was encapsulated into a gelatin capsule according to a usual method (Raw materials: safflower oil, ubiquinol, gelatin, glycerol, colorant (caramel)). The capsule allowed the intake of 100 mg of ubiquinol with one capsule (Content amount of 300 mg).
(1-3) Ubiquinol Containing Drink As a ubiquinol containing drink (comparative product 2), a drink containing 0.2% by weight of ubiquinol was prepared. As the raw materials, high-fructose corn syrup, concentrated mango juice, gelatin, collagen peptide, ubiquinol, an emulsifier, glycerol, ascorbic acid, a stabilizer (soybean polysaccharides), a green tea extract, cyclic oligosaccharide, a flavor, and a sweetener (stevia) were used. The drink allowed the intake of 100 mg of ubiquinol with 50 mL drink.
(2) Absorbability Test in Humans Humans were made to take any one of the test foods of the product of the present invention or the comparative products 1 and 2 in such a manner as that the intake amount of ubiquinol was 100 mg. Then, the ubiquinol absorbability was evaluated from the transition of the total ubiquinone concentration in blood. The test was performed to 12 male and female volunteers (six males, six females) ranging from 21 years old to 38 years old.

Based on the Declaration of Helsinki, in advance of test execution, a doctor responsible for the test gives an explanation document and a consent document for the test and then sufficiently explains the meaning and the contents of the test to the subjects, and then the doctor got the consent based on the free will of the subjects in written form.

As the test, a randomized crossover test was carried out and the absorbability of each test food was compared. The subjects were assigned at random to three groups each containing four persons, and then took each test food while dividing the period into 3 periods. Between each period, a 6 day non-test period was given. Then, all 12 subjects completed the test.

Breakfast was common to all the subjects. Immediately after taking breakfast, the subjects took each test food. Blood was collected before the intake of the test food and after the passage of 1, 2, 4, 6, 8, and 10 hours after the intake of the test food, i.e., 7 times in total, in each test period. Heparin plasma was adjusted immediately after the collection of blood.

The ubiquinol concentration in blood was measured using the obtained plasma. It has been reported that almost all of them were present as ubiquinol in blood (Non-patent Document 3). However, it is difficult to measure unstable ubiquinol. Therefore, the measurement was performed by converting ubiquinol to stable ubiquinone by oxidation treatment. The obtained ubiquinone concentration was calculated as the ubiquinol concentration. The measurement method is described below.

50 μL of p-benzoquinone (water solvent, concentration of 2 mg/mL, manufactured by Wako Pure Chemical Industries, Ltd.) was added and mixed in 200 μL of human plasma, and then allowed to stand still at room temperature for 10 minutes. Then, 1 mL of n-propanol (manufactured by Wako Pure Chemical Industries, Ltd.) was added and mixed. After centrifugation at 10,000 rpm for 10 minutes, 1 mL of supernatant was collected, and then subjected to the LC-MS analysis.

The LC separation conditions were as follows in the LC-MS analysis.

The analysis was carried out under the conditions: Pouring amount: 10 μL, Flow rate: 0.5 mL/min, Column: Unison US-C8 (manufactured by Imtakt Corporation), and A liquid: ultrapure water, B liquid: acetonitrile, and C liquid: isopropanol as the separation solvent at the linear concentration gradient of 0 minute (A liquid 20%:B liquid 80%)→15 minutes (B liquid 80%:C liquid 20%). For the MS detection, ubiquinone (Precursor ion 862.193, Product ion 219.035) was detected using 3200QTRAP (manufactured by AB SCIEX), and then the concentration was calculated in comparison with the analytical curve. The obtained concentration was defined as the ubiquinol concentration in blood.

FIG. 1 shows the transition of the change amount of the ubiquinol concentration in blood based on the concentration before the intake. FIG. 2 shows the area under the concentration in blood—time curve ($AUC_{0-10h}$). As the comparison of each food, the evaluation was performed using one sample t-test. With respect to the calculation of AUC, the area determined by the trapezoidal method based on the value before the intake was used. The numerical value is indicated by Average value±Standard deviation. The significance level of the test was set to 5% on both sides.

As shown in FIG. 1, the ubiquinol concentration in blood reached the maximum ($T_{max}$) in all the foods after the passage of 6 hours after the intake of the foods.

From FIG. 1 and FIG. 2, the maximum blood concentration ($C_{max}$) and $AUC_{0-10h}$ showed high values in the product of the present invention as compared with those of the comparative product 1. This shows that the absorbability of the ubiquinol of the product of the present invention was equal to or higher than that of the comparative product 1.

The product of the present invention exhibited significantly high ubiquinol concentration in blood when 4 hours passed after the intake as compared with that of the comparative product 1 (FIG. 1). Furthermore, when $AUC_{0-6h}$ was calculated, the $AUC_{0-6h}$ of the product of the present invention is significantly higher than that of the comparative product 1 (FIG. 3). Therefore, it was suggested that the absorbability of the ubiquinol is high.

The results above showed that the absorbability of ubiquinol of the ubiquinol containing gummy candy which is the product of the present invention is excellent.

The states of ubiquinol in the product of the present invention and the comparative products 1 and 2 were observed under an optical microscope in the same manner as in Test Example III-1. As the control, polystyrene standard beads are shown in FIG. 4.

As shown in FIG. 4, a large amount of ubiquinol is confirmed in a state of particles of 50 μm or less in the product of the present invention but, in contrast thereto, particles having a diameter of 100 μm or more are scattered in the comparative product 1. Therefore, it is expected that the absorbability of the product of the present invention into the body increases by maintaining the state of particles of 50 μm or less. Moreover, although the ubiquinol particles are very fine in the comparative product 2, there is not significant difference from the product of the present invention. It is considered that not only the particle diameter always relates to the absorbability. Moreover, from the viewpoint of portability and convenience, it can be said that the product of the present invention is superior to the comparative product 2.

Examples III-2, III-3, III-4

Gummy candy-like products were obtained in the same manner as in Example III-1 except changing the blending amount of each component. The blending amount of each component is shown in Table 4. When the obtained gummy candy products were observed under an optical microscope in the same manner as in Example Test III-1, it is found that all the particles have a size of 50 μm or less and ubiquinol is stably dispersed in the products. Moreover, all the products were health supplements which allow intake in one bite without water and delicious intake of ubiquinol.

TABLE 4

|  | Example III-1 | Example III-2 | Example III-3 | Example III-4 |
| --- | --- | --- | --- | --- |
| Ubiquinol | 2.0 | 1.0 | 14.0 | 2.0 |
| Gelatin | 6.9 | 7.5 | 9.0 | 5.2 |
| Sugar | 40.0 | 40.0 | 33.5 | 45.0 |
| Starch syrup (as solid content) | 29.0 | 29.0 | 25.0 | 31.0 |
| Ascorbic acid | 2.0 | 0.1 | 2.7 | 2.0 |
| Gallate type catechin | 0.2 | 0.1 | 0.5 | 0.2 |
| Pectin | 0.8 | 1.2 | 0.2 | 0.5 |
| Water content | 16.0 | 18.0 | 12.0 | 11.0 |
| Other components | 3.1 | 3.1 | 3.1 | 3.1 |
| Total | 100.0 | 100.0 | 100.0 | 100.0 |

(Unit: % by weight)

The invention claimed is:

1. A gel-like composition in which ubiquinol is dispersed and stabilized in a gel, the gel-like composition comprising:
   0.2 to 15% by weight of ubiquinol;
   5 to 15% by weight of gelatin;
   55 to 80% by weight of carbohydrate and/or water-soluble dietary fiber; and
   9 to 18% by weight of water, and further comprising:
   ascorbic acid and/or gallate type catechin.

2. The gel-like composition according to claim 1 comprising:
   1 to 15% by weight of ubiquinol;
   5 to 12% by weight of gelatin;
   55 to 80% by weight of carbohydrate and/or water-soluble dietary fiber;
   9 to 18% by weight of water; and
   0.01 to 4% by weight of ascorbic acid and/or gallate type catechin.

3. The gel-like composition according to claim 1 comprising:
1 to 5% by weight of ubiquinol;
5 to 12% by weight of gelatin;
60 to 76% by weight of carbohydrate and/or water-soluble dietary fiber; and
13 to 18% by weight of water.

4. The gel-like composition according to claim 1 further comprising organic acid and flavor.

5. The gel-like composition according to claim 1, wherein a content of an emulsifier and a content of oils and fats are less than 1% by weight.

6. The gel-like composition according to claim 1 comprising 0.1 to 2.0% by weight of pectin.

7. The gel-like composition according to claim 1, wherein the ubiquinol is dispersed in the gel with an average particle diameter of 50 μm or less.

8. The gel-like composition according to claim 1, wherein a weight ratio of ubiquinol/ubiquinone after the gel-like composition is allowed to stand at 37° C. in the air for 7 days is 99/1 or more.

9. The gel-like composition according to claim 1, wherein the weight ratio of ubiquinol/ubiquinone after the gel-like composition is allowed to stand under an atmosphere of 40° C. and a humidity of 75% for 6 months is 95/5 or more.

10. The gel-like composition according to claim 1, wherein a form of the gel-like composition is a gummy candy which is designed in such a manner that a weight of one piece is 1.0 to 4.0 g.

11. A method for producing the gel-like composition according to claim 1 at least containing ubiquinol, gelatin, carbohydrate and/or water-soluble dietary fiber, gelatin, and ascorbic acid and/or gallate type catechin, the method comprising:
(I) a step of heating and dissolving carbohydrate and/or water-soluble dietary fiber, and gelatin in water to prepare a dough;
(II) a step of preparing a fluid liquid containing ubiquinol and gelatin and further containing ascorbic acid and/or gallate type catechin; and
(III) a step of mixing the dough and the fluid liquid.

12. The method for producing a gel-like composition according to claim 11, comprising:
a step of stiffing and mixing ubiquinol melted at 46° C. or higher in presence of at least gelatin, and pulverizing the ubiquinol until an average particle diameter of ubiquinol reaches 50 μm or less.

* * * * *